(12) United States Patent
Nakamura et al.

(10) Patent No.: US 8,658,132 B2
(45) Date of Patent: *Feb. 25, 2014

(54) METHOD FOR PRODUCTION OF RADIATION DIAGNOSTIC IMAGING AGENT

(75) Inventors: Daisaku Nakamura, Sodegaura (JP); Soichi Nakamura, Sodegaura (JP); Masahito Toyama, Sodegaura (JP); Akio Hayashi, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/565,204

(22) Filed: Aug. 2, 2012

(65) Prior Publication Data

US 2012/0301399 A1 Nov. 29, 2012

Related U.S. Application Data

(62) Division of application No. 12/526,667, filed as application No. PCT/JP2008/052231 on Feb. 12, 2008, now Pat. No. 8,343,459.

(30) Foreign Application Priority Data

Feb. 13, 2007 (JP) ................................. 2007-031692

(51) Int. Cl.
*A61K 51/00* (2006.01)
*A61M 36/14* (2006.01)

(52) U.S. Cl.
USPC ....... 424/1.89; 424/1.11; 424/1.65; 424/1.81; 424/1.85

(58) Field of Classification Search
USPC ............ 424/1.11, 1.65, 1.81, 1.85, 1.89, 9.1, 424/9.3, 9.4, 9.5, 9.6, 9.7, 9.8; 548/950
See application file for complete search history.

(56) References Cited

U.S. PATENT DOCUMENTS

| | | | |
|---|---|---|---|
| 4,727,145 A | 2/1988 | Press | |
| 4,791,117 A | 12/1988 | Press | |
| 4,833,149 A | 5/1989 | Press | |
| 4,871,745 A | 10/1989 | Press | |
| 5,658,857 A | 8/1997 | Andree et al. | |
| 5,808,146 A | 9/1998 | Goodman et al. | |
| 5,817,776 A | 10/1998 | Goodman et al. | |
| 6,027,710 A | 2/2000 | Higashi et al. | |
| 6,045,773 A | 4/2000 | Isakson et al. | |
| 6,562,579 B1 | 5/2003 | Yu et al. | |
| 6,596,731 B2 | 7/2003 | Mutel et al. | |
| 6,713,042 B2 | 3/2004 | Liu | |
| 7,186,714 B2 | 3/2007 | Gudmundsson et al. | |
| 7,264,792 B2 | 9/2007 | Gibson et al. | |
| 7,425,318 B2 | 9/2008 | Kung et al. | |
| 7,563,433 B2 | 7/2009 | McBride et al. | |
| 7,714,115 B2 * | 5/2010 | Grigg et al. | 536/18.4 |
| 8,343,459 B2 * | 1/2013 | Nakamura et al. | 424/1.89 |
| 2001/0051632 A1 | 12/2001 | Chai et al. | |
| 2002/0042420 A1 | 4/2002 | Briem et al. | |
| 2002/0188128 A1 | 12/2002 | Mutel et al. | |
| 2003/0212096 A1 | 11/2003 | Mutel | |
| 2005/0169837 A1 | 8/2005 | Auberson | |
| 2005/0175536 A1 | 8/2005 | Knight Castro | |
| 2005/0182059 A1 | 8/2005 | Wizenberg | |
| 2006/0051293 A1 | 3/2006 | Kung et al. | |
| 2006/0292073 A1 | 12/2006 | Goodman et al. | |
| 2008/0076914 A1 | 3/2008 | Grigg et al. | |
| 2008/0193379 A1 | 8/2008 | Shimada et al. | |
| 2009/0252679 A1 | 10/2009 | Tanifuji et al. | |
| 2010/0249418 A1 | 9/2010 | Tanifuji et al. | |
| 2010/0249419 A1 | 9/2010 | Tanifuji et al. | |
| 2010/0292479 A1 | 11/2010 | Tanifuji et al. | |

FOREIGN PATENT DOCUMENTS

| | | |
|---|---|---|
| CN | 1117732 A | 2/1996 |
| CN | 1518550 A | 8/2004 |
| CN | 1529597 A | 9/2004 |
| CN | 1646175 A | 7/2005 |
| EP | 0261912 A2 | 3/1988 |
| EP | 0832654 A2 | 4/1998 |
| EP | 2 080 526 A1 | 7/2009 |

(Continued)

OTHER PUBLICATIONS

Appendix A: McBride, U.S. Appl. No. 11/960,262, filed Dec. 19, 2007.

(Continued)

*Primary Examiner* — D L Jones
(74) *Attorney, Agent, or Firm* — Fitch, Even, Tabin & Flannery LLP

(57) ABSTRACT

A method for producing a radioactive diagnostic imaging agent containing a radioactive $^{18}$ fluorine-labeled organic compound represented by the following formula (1):

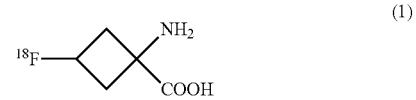

(1)

as an effective ingredient in which radiolysis of the effective ingredient is inhibited, involves providing a solution containing the radioactive $^{18}$fluorine-labeled organic compound represented by the above formula (1), adding an acid to the solution obtained in the first step in an amount sufficient for the solution to be kept within a pH of 2.0-5.9 in the following third step, and diluting the solution obtained in the second step in order to adjust the solution to a desired radioactive concentration within a pH of 2.0-5.9.

5 Claims, 1 Drawing Sheet

(56) References Cited

FOREIGN PATENT DOCUMENTS

| JP | 63-91391 A | 4/1988 |
|---|---|---|
| JP | 10-147542 A | 6/1998 |
| JP | 2000-500442 T | 1/2000 |
| JP | 2001-043978 A | 2/2001 |
| JP | 2002-523383 A | 7/2002 |
| JP | 2004-506633 A | 3/2004 |
| JP | 2004-506723 A | 3/2004 |
| JP | 2004-525192 A | 8/2004 |
| JP | 2005-504055 A | 2/2005 |
| JP | 2005-512945 A | 5/2005 |
| JP | 2005-526749 A | 9/2005 |
| JP | 2006-500319 A | 1/2006 |
| JP | 2006-510706 A | 3/2006 |
| JP | 2006-304338 A | 11/2006 |
| WO | 97/17092 A1 | 5/1997 |
| WO | 00/10614 A1 | 3/2000 |
| WO | 01/74813 A2 | 10/2001 |
| WO | 01/74815 A1 | 10/2001 |
| WO | 02/16333 A2 | 2/2002 |
| WO | 02/092086 A | 11/2002 |
| WO | 03/018070 A1 | 3/2003 |
| WO | 03/090789 A1 | 11/2003 |
| WO | 2004/043497 A1 | 5/2004 |
| WO | 2005/066177 A1 | 7/2005 |
| WO | 2006/037950 A1 | 4/2006 |
| WO | 2006/134822 A1 | 12/2006 |
| WO | 2007/001958 A2 | 1/2007 |
| WO | 2007/132689 A1 | 11/2007 |
| WO | 2008/075522 A1 | 6/2008 |

OTHER PUBLICATIONS

Appendix B: McBride, U.S. Appl. No. 60/884,521, filed Jan. 11, 2007.
Office Action dated Dec. 4, 2012 in JP Patent Application No. 2008-558082.
CN Office Action dated Aug. 20, 2013, issued against corresponding CN Application No. 200880008655.6 (partial English, 7 pages).
International Search Report dated Mar. 11, 2008, corresponding with International Application PCT/JP2008/052231.
McConathy et al., "Improved Synthesis of Anti-[18F]FACBC: improved preparation of labeling precursor and automated radiosynthesis", Applied Tadiation and Isotopes, vol. 58, No. 6, (2003), pp. 657-666.
Shuntaro Oka et al., "A Preliminary Study of Anti-1-Amino-3-18F-Fluorocyclobutyl-1-Carboxylic Acid for the Detection of Prostate Cancer", The Journal of Nuclear Medicine, vol. 48, No. 1, Jan. 2007, pp. 46-55.
Pharmaceutical Affairs Bureau Notification No. 0624001, pp. 1-17.
Israel Office Action, dated Oct. 9, 2011, Ministry of Justice Patent Office, corresponding with Israel Patent Application No. 198995.
John A. Hardy et al., "Alzheimer's Disease: The Amyloid Cascade Hypothesis", Science, vol. 256, Apr. 10, 1992, pp. 184-185.
Guy McKhann, MD et al., "Clinical diagnosis of Alzheimer's disease: Report of the NINCDS-ADRDA Work Group under the auspices of Department of Health and Human Services Task Force on Alzheimer's Disease", Neurology, vol. 34, Jul. 1984, pp. 939-944.
Z.P. Zhuang et al., "Radioiodinated Styrylbenzenes and Thioflavins as Probes for Amyloid Aggregates", J. Med. Chem., vol. 44, No. 12, 2001, pp. 1905-1914.
Masahiro Ono et al., "C-labeled stilbene derivatives as Aβ-aggregate-specific PET imaging agents for Alzheimer's disease", Elsevier, Nuclear Medicine and Biology, vol. 30, 2003, pp. 565-571.
Hank F. Kung et al., "Novel Stilbenes as Probes for Amyloid Plaques", J. Am. Chem. Soc., vol. 123, 2001, pp. 12740-12741.
Zhuang et al., "IBOX(2-(4'-dimethylaminophenyl)-6-iodobenzoxazole): a ligand for imaging amyloid plaques in the brain", Elsevier, Nuclear Medicine and Biology, vol. 28, 2001, pp. 887-894.
S. Furumoto et al., "[11C]BF-227: A New 11C-Labeled 2-Ethenylbenzoxazole Derivative for Amyloid-B Plaques Imaging", European Journal of Nuclear Medicine and Molecular Imaging, vol. 32, Sup. 1, 2005, p. 759.

Eric D. Agdeppa, PhD et al., "2-Dialkylamino-6-Acylmalononitrile Naphthalenes (DDNP Analogs): Novel Diagnostic and Therapeutic Tools in Alzheimer's Disease", Elsevier, Molecular Imaging and Biology, vol. 5, No. 6, 2004, pp. 404-417.
Zhuang et al., "Structure-Activity Relationship of Imidazo [1,2-a]pyridines as Ligands for Detecting β-Amyloid Plaques in the Brain", J. Med. Chem., vol. 46, 2003, pp. 237-243.
William E. Klunk, MD et al., "Imaging Brain Amyloid in Alzheimer's Disease with Pittsburgh Compound-B", American Neurological Association, vol. 55, No. 3, Mar. 2004, pp. 306-319.
Nicolaas Verhoeff, MD et al., "In-Vivo Imaging of Alzheimer Disease β-Amyloid With [11C]SB-13 PET", American Journal of Geriatric Psychiatry, vol. 12:6, 2004, pp. 584-595.
Skovronsky et al., "In vivo detection of amyloid plaques in a mouse model of Alzheimer's disease", Proc. National Academy Science, vol. 97, No. 13, Jun. 20, 2000, pp. 7609-7614.
Newberg et al., "Safety, Biodistribution, and Dosimetry of 123l-IMPY: A Novel Amyloid Plaque-Imaging Agent for the Diagnosis of Alzheimer's Disease", The Journal of Nuclear Medicine, vol. 47, No. 5, May 2006, pp. 748-754.
Young Soo Chang et al., "Synthesis and evaluation of benzothiophene derivatives as ligands for imaging β-amyloid plaques in Alzheimer's disease", Elsevier, Nuclear Medicine and Biology, vol. 33, 2006, pp. 811-820.
Lisheng Cai et al., "Synthesis and Evaluation of Two 18F-Labeled 6-Iodo-2-(4'-N,N-dimethylamino)phenylimidazo[1,2-a]pyridine Derivatives as Prospective Radioligands for β-Amyloid in Alzheimer's Disease", Journal of Medicinal Chemistry, vol. 47, No. 9, 2004, pp. 2208-2218.
Masahiro Ono et al., Benzofuran derivatives as Aβ-aggregate-specific imaging agents for Alzheimer's disease, Elsevier, Nuclear Medicine and Biology, vol. 29, 2002, pp. 633-642.
Maud Hervet et al., "Comparative Study on the Reactivity of 6-Haloimidazo[1,2-a]pyridine Derivatives towards Negishi-and Stille-Coupling Reactions", Helvetica Chimica Acta, vol. 86, 2003, pp. 3461-3469.
Jerzy Lange et al., "A Structure-Activity Relationship Study of the Affinity of Selected Imidazo[1,2-a]Pyridine Derivatives, Congeners of Zolpidem, for the w1-Subtype of the Benzodiazepine Receptor" Acta Poloniae Pharamaceutica—Drug Research, vol. 58, No. 1, 2001, pp. 43-52.
Andrew Katsifis et al., "Synthesis of [123I]N',N'-Dimethyl-6-Methyl-(4'-Iodophenyl)Imidazo[1,2-a]Pyridine-3-acetamide for the Study of Peripheral Benzodiazepine Receptors using SPECT", Journal of Labelled Compounds and Radiopharmaceuticals, vol. 43, 2000, pp. 385-394.
Gordon B. Barlin et al., "Imidazo[1,2-b]pyridazines, XX*T Syntheses of Some 3-Acylaminomethyl-6-(chloro, fluoro, methoxy, methylthio, phenoxyand phenylthio)-2-(phenyl, 4-t-butylphenyl, 4-cyclohexlphenyl, B-naphthyl and styryl)imidazo[1,2-b]pyridazines and Their Interaction with Central and Peripheral-Type Benzodiazepine Receptors", Australian Journal of Chemistry, vol. 49, No. 4, 1996, pp. 451-461.
A. Katsifis et al., "Synthesis of [123I]iodine labelled imidazo[1,2-b]pyridazines as potential probes for the study of peripheral benzodiazepine receptors using SPECT", Radiochim Acta, vol. 92, 2004, pp. 305-309.
Gordon B. Barlin, "Imidazo[1,2-b]pyridazines: Syntheses and Interaction with Central and Peripheral-Type (Mitochonodrial) Benzodiazepine Receptors", J. Heterocyclic Chem., vol. 35, Sep.-Oct. 1998, pp. 1205-1217.
Danqian Xu et al., Short Paper, "Synthesis of 2-arylimidazo[1,2-a]pyrimidines by the Chichibabin synthesis in ionic liquids", J. Chem., Research (S), 2003, pp. 645-647.
Sundberg et al., "Preparation of 2-Aryl and 2-Aryloxymethyl Imidazo[1,2-a]pyridines and Related Compounds", Journal of Heterocyclic Chemistry, vol. 25, No. 1, 1988, pp. 129-137.
Enguehard et al., J. Org. Chem, vol. 68, 2003, pp. 4367-4370.
Chandra Shah et al, "Novel Human Histamine H3 Receptor Antagonist", Bioorganic & Medicinal Chemistry Letters, vol. 12, 2002, pp. 3309-3312.

(56) References Cited

OTHER PUBLICATIONS

Pauline J. Sanfilippo et al., "Synthesis of (Aryloxy)alkylamines. 2. Novel Imidazo-fused Heterocycles with Calcium Channel Blocking and Local Anesthetic Activity", Journal of Medicinal Chemistry, vol. 31, No. 11, 1988, pp. 2221-2227.
International Search Report dated Dec. 4, 2007, corresponding with International Application PCT/JP2007/071121.
Chun-xiong Lu et al., Synthesis and Biodistribution of B Amyloid Plaques Imaging Agent 131I-IMPY, Journal of Nuclear and Radiochemistry, vol. 27, No. 4, Nov. 2005, pp. 232-235 (abstract at p. 235).
CN Office Action dated Nov. 24, 2011, issued against CN Application 200880123407.6 (also see U.S. Appl. No. 12/740646).
Examination Report dated Sep. 26, 2011, issued against Australian Application 2007252658.
CN Office Action dated Nov. 8, 2011, issued against CN Application 200780048027.6.
US Office Action dated Apr. 23, 2012, issued in U.S. Appl. No. 12/526,667.
CN Office Action dated Jan. 18, 2012, issued against CN Application 200880121562.4.
European Patent Office Communication dated May 3, 2011, issued against European Application 08711095.3.
CN Office Action dated Mar. 22, 2011, issued against CN Application 200880008655.6.
Taiwanese Office Action issued against corresponding Taiwanese Application No. TW20080104810, entire document, 4 pages.

* cited by examiner

METHOD FOR PRODUCTION OF RADIATION DIAGNOSTIC IMAGING AGENT

CROSS-REFERENCE TO RELATED APPLICATIONS

This application is a Divisional Patent Application of U.S. application Ser. No. 12/526,667, filed Aug. 11, 2009, which is the U.S. National Stage (371) application of PCT International Application No. PCT/JP2008/052231 filed Feb. 12, 2008, and claims the benefit of foreign priority under 35 U.S.C. §119 based on Japanese Application No. 2007-031692 filed Feb. 13, 2007, the complete disclosures of all of the aforesaid applications are incorporated herein by reference.

TECHNICAL FIELD

The present invention relates to a method for producing a radioactive diagnostic imaging agent containing a radioactive halogen-labeled organic compound as an effective ingredient. More specifically, it relates to a method for producing a radioactive diagnostic imaging agent, which can inhibits radiolysis of the radioactive halogen-labeled organic compound.

BACKGROUND ART

The radioactive diagnostic imaging agent is a medicine directly administered to a human body and is a pharmaceutical composition containing a compound labeled with a specific radioisotope as an effective ingredient. The radioactive diagnostic imaging agent enables diagnosis by administering an agent to a subject and detecting a radiation emitted from the compound, followed by imaging based on information obtained from the radiation. The thus-conducted diagnosing method is referred to as nuclear medicine examination, and is effective in diagnosing a variety of diseases including heart disease and cancer. Also, nuclear medicine examination is characteristic in that it has not only high specificity and sensitivity to diseases, but also has an advantage of providing information on the functionality of lesions, compared to other examination techniques.

Compounds which are researched and developed for radioactive diagnostic imaging agents include 3-[$^{18}$F] fluoro-1-aminocyclobutanecarboxylic acid (hereinafter referred to as [$^{18}$F] FACBC). It is known that [$^{18}$F] FACBC is taken up into a cell via an amino acid transporter. Thus [$^{18}$F] FACBC is expected to be developed as a tumor diagnostic agent since it is largely taken up into tumor cells which are highly proliferative and active in protein synthesis.

In radioactive diagnostic imaging agents, a problem often arises such that compounds decompose by self-radiation during delivery of the agents so as to cause decrease in radiochemical purity due to so-called radiolysis. For general pharmaceuticals, it is recommended in the guideline of ICH that if decomposed matters in an agent exceed 1.0%, the decomposed matters be subjected to structure determination when the maximum daily dosage of an effective component thereof is as small as not more than 1 mg (Non-Patent Document 1). However, for radiopharmaceuticals low in a blended amount per se in the agent, in most cases, the physical amount of impurities resulting from the radiolysis in the agent is as small as about $10^{-12}$ mol, even if it exceeds 1.0%. Thus, it is very difficult to presume a structure of the decomposed matters, and to conduct verification as to whether or not the decomposed matters affect effectiveness such as tumor accumulation of the agent.

Also, particularly in radioactive diagnostic imaging agents, if impurities are generated due to decomposition, they often significantly affect the resulting image, even if the generated amount thereof is a small amount. Therefore, impurities in the radioactive diagnostic imaging agent should be maintained as low as possible, and it is preferable that radiolysis which may cause the production of impurities should also be inhibited as much as possible.

Various methods for inhibiting radiolysis have been examined focusing on application to [$^{18}$F] fluoro-deoxyglucose (hereinafter referred to as [18F] FDG).

International Publication No. WO03/090789 pamphlet discloses a method of reducing the radiolysis of [$^{18}$F] FDG by adding a weak acid-based buffer to a [$^{18}$F] FDG solution and an injection prepared by the method (Patent Document 1). Also, International Publication No. WO04/043497 pamphlet discloses adding ethanol to a [$^{18}$F] FDG solution to obtain a composition for injection which may be reduced in radiolysis of [$^{18}$F] FDG to improve stability (Patent Document 2).

Japanese Patent Laid-open (Kokai) No. H10-147542 discloses a technique utilizing an organic compound high in physiological acceptability such as monosaccharides, disaccharides, organic acids and salts or esters thereof as a radiation protecting agent (Patent Document 3). In this publication, the organic compound high in physiological acceptability and particularly effective as the radiation protecting agent is defined to have a reaction rate constant with OH radicals, H radicals or hydrated electrons in the range of $1 \times 10^8$ to $5 \times 10^{10}$ mol$^{-1}$ s$^{-1}$.

International Publication No. WO06/134822 pamphlet discloses a radioactive diagnostic imaging agent reduced in radiolysis by blending various sugar or sugar alcohol.

Non-Patent Document 1: Pharmaceutical Affairs Bureau Notification No. 0624001 (page 12)
Patent Document 1: International Publication No. WO03/090789 pamphlet
Patent Document 2: International Publication No. WO04/043497 pamphlet
Patent Document 3: Japanese Patent Laid-open (Kokai) No. H10-147542
Patent Document 4: International Publication No. WO06/134822 pamphlet

DISCLOSURE OF THE INVENTION

Problems to be Solved by the Invention

As described above, International Publication No. WO03/090789 pamphlet and International Publication No. WO04/043497 pamphlet disclose conditions for preventing radiolysis of [$^{18}$F] FDG in the solution. However, these documents only disclose techniques for reducing radiolysis of [$^{18}$F] FDG only, but do not disclose any technique for reducing radiolysis of a series of radioactive fluorine-labeled amino acid compounds such as [$^{18}$F] FACBC.

Japanese Patent Laid-open (Kokai) No. H10-147542 discloses a technique utilizing an organic compound high in physiological acceptability as a radiation protecting agent for radiopharmaceuticals. However, it is not apparent which compound is selected as the organic compound high in physiological acceptability or how much the compound is added in order to prevent radiolysis of the series of radioactive fluorine-labeled amino acid compounds such as [$^{18}$F] FACBC.

International Publication No. WO06/134822 pamphlet discloses a technique inhibiting radiolysis by blending various sugar or sugar alcohol with a radioactive diagnostic imaging agent. However, this publication also fails to disclose a condition for effectively inhibiting radiolysis of the series of radioactive fluorine-labeled amino acid compounds such as [$^{18}$F] FACBC.

The present inventors have found that radiolysis can be reduced by adding a sugar lactone to a radioactive diagnostic imaging agent containing [$^{18}$F] FACBC as an effective ingredient, and thus have filed a patent application (Japanese Patent Application No. 2006-304338). This invention is very useful in that an effective amount of the sugar lactone has been found for inhibiting radiolysis of [$^{18}$F] FACBC.

However, since the sugar lactone is a compound having a cyclic ester in its molecule, it is hydrolyzed when it is used as an injection such as a radioactive diagnostic imaging agent. This problem cannot be avoided for sugar lactone. Also, ascorbic acid which is one of the sugar lactone is a compound which has a double bond in its molecule so as to exhibit a reducing action and thus can easily be oxidized by dissolved oxygen or the like. Thus, the use thereof requires removing oxygen as much as possible, and is problematic in that handling operation may become complicated.

The present invention has been made in view of the above circumstances, and has aimed at providing a method for producing a radiopharmaceutical containing a radioactive halogen-labeled amino acid compound as an effective ingredient as an injection having a composition which can inhibit radiolysis of the effective ingredient so as to further improve stability.

Means for Solving the Problem

As a result of investigations, the present inventors have found that the radiolysis of [$^{18}$F] FACBC is reduced dependently upon pH. Particularly, it has been found that when the pH value is not more than 5.9, stability thereof is maintained even if there exist no pharmaceutical additives or buffers that prevent radiolysis, as opposed to the conventional knowledge.

The present inventors have also found that the radiolysis can be additionally reduced by adding a pharmaceutical additive that inhibits the radiolysis.

Based on these information, it has been found that the radiolysis during the production step and even after the preparation of the agent can be reduced by adding a certain amount of acid and optionally a pharmaceutical additive to a [$^{18}$F] FACBC solution which has not been subjected to concentration adjustment during the production step.

According to the present invention, a method for producing a radioactive diagnostic imaging agent, comprising a solution preparation step of preparing a solution containing a radioactive fluorine-labeled organic compound represented by the following formula (1):

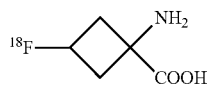

(1)

and, a dilution step of diluting the solution containing the radioactive fluorine-labeled organic compound in order to adjust radioactive concentration thereof, which further comprises an acid addition step of adding an acid to the solution containing the radioactive fluorine-labeled organic compound, after the solution preparation step, and before the dilution step, wherein the acid is added in the acid addition step in an amount sufficient to adjust the pH of the solution resulting from the dilution step to 2.0-5.9. The addition amount of acid is preferably 0.40-2.8 mmol per 1 L of the solution resulting from the dilution step, and more preferably 0.52-2.8 mmol per 1 L of the solution resulting from the dilution step.

As an acid to be added in the acid addition step, can used an acid having physiological acceptability. Preferably, ascorbic acid, benzoic acid, hydrochloric acid, acetic acid, citric acid, gentisic acid, oxalic acid and the like can be used, more preferably, ascorbic acid, hydrochloric acid or gentisic acid can be used, and particularly preferably, hydrochloric acid can be used.

The diluting step in the present invention is conducted, for example, by adding water, a physiological saline solution or a Ringer's solution to the solution containing the radioactive fluorine-labeled organic compound.

Sugar or sugar alcohol may be further added as an additive agent in each of the acid addition step and the dilution step. In this instance, as sugar and sugar alcohol to be added, various compounds can be used, and preferable sugar alcohol includes erythritol xylitol, sorbitol or mannitol. Addition amount of sugar or sugar alcohol is preferably adjusted to an amount that meets a concentration of not less than 0.5 mmol/L in the solution resulting from the dilution step.

Meanwhile, the amount of sugar or sugar alcohol does not have any upper limit from the viewpoint of inhibition of radiolysis, but form the viewpoint of safety in use for injection, it should be maintained to be not more than a certain concentration. First, the amount of sugar or sugar alcohol needs to be within a range that is acceptable for additive agents for injection, that is, the total dose thereof needs to be not more than an amount that is acceptable for pharmaceutical additives. This range is determined in consideration of an acceptable daily dose of each additive agent. For example, the maximum dose each of sugar and sugar alcohol reported in a literature in case of intravenous administration is mannitol: 1.2 g, xylitol: 200 mg, sorbitol: 1.5 g, glucose: 8 g, fructose: 900 mg, martose: 10 g, and lactose: 1250 mg ("Japanese Pharmaceutical Excipients Directory 2000" edited by Japanese Pharmaceutical Excipients Council, YAKUJI NIPPO, LTD., 2000). Therefore, in order to blend these sugars or sugar alcohols as additives, the addition amount is set so that the final dosage contained in the injection does not exceed this maximum dose. On the other hand, for use in injection, physical properties of injections including osmotic pressure and viscosity must be taken into consideration. For example, when they are blended with an injection intravenously administered in an amount of about 2.5-5.0 mL at a time, it may be blended at a concentration of not more than 50 mmol/L, more preferably not more than 20 mmol/L.

Effect of the Invention

According to the present invention, an acid and optionally a sugar or sugar alcohol are added to a radioactive diagnostic imaging agent containing a radioactive halogen-labeled amino acid compound as an effective ingredient in the production process thereof, and thus radiolysis of the effective ingredient can be inhibited during production and storage, thereby further improving stability.

BEST MODE FOR CARRYING OUT THE INVENTION

Hereinafter, a preferable embodiment of the method for producing a radioactive diagnostic imaging agent according to the present invention will be described, taking the case of producing a [$^{18}$F] FACBC injection.

A method for producing a radioactive diagnostic imaging agent according to the preferable embodiment is a method comprising a solution preparation step of preparing a solution containing a radioactive fluorine-labeled organic compound, an acid addition step of adding an acid to the solution containing a radioactive fluorine-labeled organic compound, and a dilution step of diluting a solution resulting from the acid addition step to adjust its radioactive concentration.

The solution preparation step of preparing the radioactive fluorine-labeled organic compound containing solution comprises; a step of imparting a radioactive fluorine to a precursor (Step 1); a step of conducting deprotection of a compound to which a radioactive fluorine has been imparted (Step 2); and a step of conducting purification of a solution containing [$^{18}$F] after the deprotection (Step 3).

Radioactive fluorine used for labeling can be obtained by a known method, for example, a method in which $H_2^{18}O$ enriched water is used as a target and exposed to proton bombardment. In this instance, radioactive fluorine exists in the $H_2^{18}O$ enriched water used as a target. The $H_2^{18}O$ enriched water containing radioactive fluorine is allowed to pass through, for example, an anion-exchange column so that the radioactive fluorine is adsorbed and collected on the column, thereby being separated from the $H_2^{18}O$ enriched water. Thereafter, a potassium carbonate solution is allowed to pass through the column to elute the radioactive fluorine, and the eluate is supplemented with a phase transfer catalyst and is evaporated to dryness, thereby activating the radioactive fluorine.

In step 1, the mixture containing the dried radioactive fluorine is dissolved in acetonitrile, and cis-1-(N-tert-butoxycarbonyl)amino-3-[(trifluoromethyl)sulfonyloxy]cyclobutane carboxylic acid ethyl ester, as a precursor, is added to the acetonitrile solution to allow them to react under heating. As a result, radioactive fluorine is added to the precursor, whereby trans-1-(N-tert-butoxycarbonyl)amino-3-[$^{18}$F] fluorocyclobutane carboxylic acid ethyl ester is synthesized.

In step 2, the solution of trans-1-(N-tert-butoxycarbonyl)amino-3-[$^{18}$F] fluorocyclobutane carboxylic acid ethyl ester obtained in step 1 is subjected to deprotection and deesterification to yield a solution containing [$^{18}$F] FACBC as a target product. This step can be conducted by various methods, for example, a method of giving an acidic condition to the reaction solution. In this instance, the acidic condition can be given by various methods, for example, a method of adding hydrochloric acid to a solution containing trans-1-(N-tert-butoxycarbonyl)amino-3-[$^{18}$F] fluorocyclobutane carboxylic acid ethyl ester. The amount of acid to be added is not particularly restricted as long as the amount can provide an acidic condition sufficient for the deprotection.

In step 3, purification of the solution containing [$^{18}$F] FACBC which is obtained in step 2 is performed. The purification process to be used includes various processes such as a liquid-liquid extraction process and a column separation process. For example, a process in which the reaction solution is injected into HPLC to obtain a fraction containing [$^{18}$F] FACBC and a process in which various solid phase columns are used can be used. The [$^{18}$F] FACBC solution can be obtained in this step, and thus the solution preparation step of preparing a radioactive fluorine-labeled compound containing solution is completed.

After the solution preparation step of preparing a radioactive fluorine-labeled compound containing solution has been completed, an acid addition step is conducted. This step is conducted by adding an acid in an amount sufficient to have a radiolysis inhibition effect to the [$^{18}$F] FACEC solution which is obtained in the above solution preparation step. Since the acid is added for the purpose of adjusting the pH of the radioactive diagnostic imaging agent, various acids acceptable for pharmaceutical additives can be used as the acid. Examples of acids preferably used include ascorbic acid, benzoic acid, hydrochloric acid, acetic acid, citric acid, gentisic acid and oxalic acid, and more preferably ascorbic acid, hydrochloric acid or gentisic acid is used, and particularly preferably hydrochloric acid is used. The amount of an acid to be added is an amount sufficient to make the pH of the solution after the dilution step to 2.0-5.9, and more preferably to 2.0-4.9, and preferably an amount corresponding to 0.40-2.8 mmol per 1 L of the radioactive diagnostic imaging agent resulting from the dilution step described later. For example, when the amount of solution resulting from the dilution step is 75 mL, the acid corresponding to 0.030-0.21 mmol (that is, 0.30-2.1 mL when the acid to be added has a concentration of 0.1 mol/L) may be added.

Meanwhile, the amount of solution resulting from the dilution step can be readily determined by methods usually employed by the skilled in the art. For example, it can be readily determined by a method in which the radioactive concentration of the [$^{18}$F] FACBC solution obtained in the above solution preparation step is divided by a radioactive concentration of the target agent, followed by multiplying the obtained quotient by the amount of the [$^{18}$F] FACBC solution obtained in the above solution preparation step.

After the acid addition step has been completed, the dilution step is conducted to obtain a radioactive diagnostic imaging agent as a target compound in the method for production of the present invention. The dilution step can be conducted by adding water, a physiological saline solution or a Ringer's solution so as to make the amount of solution determined as above. After the completion of the dilution step, the solution can be aliquoted in an aimed amount in a vial for use as the radioactive diagnostic imaging agent.

Meanwhile, when a radioactive diagnostic imaging agent further comprising sugar or sugar alcohol is prepared, sugar or sugar alcohol may be added to the [$^{18}$F] FACBC solution in the acid addition step and/or the dilution step. Sugar or sugar alcohol can be added in a various form such as a solution, powder or crystal, but is preferably added in a form of solution from the viewpoint of workability.

The radioactive diagnostic imaging agent obtained by the present invention should have a radioactivity enabling PET imaging when it is used. For example, with the aim of performing PET imaging on adults, it should have a radioactivity of 50-225 MBq when it is used.

The obtained radioactive diagnostic imaging agent can be used in the same manner as other generally-known radioactive diagnostic imaging agents. Specifically, it can be administered intravenously or locally to a subject. Distribution of the administered agent can be imaged by using a PET device in accordance with a conventional method.

EXAMPLE

Hereinafter, the present invention is described in more detail by way of Examples and Reference Examples. However, the present invention is not limited to these Examples.

Examples 1-7

[$^{18}$F]fluoride ion-containing H$_2$$^{18}$O (with a radioactivity of 138-158 GBq at the initiation of production, see Table 1) was allowed to pass through an anion-exchange column to adsorb and collect [$^{18}$F]fluoride ion on the column. Then, the column was washed with water, and a mixed solution composed of [$^{18}$F]fluoride ion, a potassium carbonate solution and a phase transfer catalyst was obtained in accordance with an ordinary method (for example, a method described in the references (Radioisotopes, 50, (2001), p. 205-227; Radioisotopes, 50, (2001), p. 228-256; "Production and quality control of radioactive agents for PET—Handbook of synthesis and clinical use—(2$^{nd}$ edition)", edited by PET Chemistry Workshop).

After the obtained mixed solution was heated in a reaction vessel to evaporate water to dryness, a solution of qis-1-(N-tert-butoxycarbonyl)amino-3-[(trifluoromethyl)sulfonyloxy]-cyclobutane carboxylic acid ethyl ester in acetonitrile was added thereto. The obtained solution was heated so as not to evaporate acetonitrile, thereby allowing nucleophilic substitution reaction to proceed to obtain a [$^{18}$F] fluorine-labeled compound.

After the reaction vessel was cooled to about 40° C., water was added to the reaction solution for dilution, and the mixture was passed through a reversed phase column to collect the [$^{18}$F] fluorine-labeled compound. This column was washed with water, and flashed with a flow of helium gas. Then, the column was charged with a sodium hydroxide solution, and an alkali solution was eluated from the column and collected in a vial. This operation was repeated twice. Then, the column was washed with water, and then the washing was combined with the above-collected alkali solutions.

Next, to the above-collected solution, hydrochloric acid was added, and the mixture was heated to effect deprotection reaction. The mixture was then passed through an ion retardation column, an alumina column and a reversed phase column in this order to perform purification and obtain a stock solution of [$^{18}$F] FACBC. The radioactivity and the solution amount of the obtained stock solution of [$^{18}$F] FACBC were shown in Table 1.

TABLE 1

Radioactivity used in each experiment, and radioactivity and amount of [$^{18}$F] FACBC stock solution

|  | Initial | [$^{18}$F] FACBC stock solution | |
| --- | --- | --- | --- |
|  | radioactivity [GBq] | Radioactivity* [GBq] | Amount of solution [mL] |
| Example 1 | 138 | 32.1 | 14.7 |
| Example 2 | 155 | 38.3 | 14.8 |
| Example 3 | 151 | 34.0 | 15.6 |
| Example 4 | 152 | 30.3 | 15.2 |
| Example 5 | 156 | 37.1 | 15.3 |
| Example 6 | 158 | 40.6 | 15.6 |
| Example 7 | 150 | 38.4 | 14.7 |

*value expected 2 hours after the initiation of production

To a 16.5 mL vial, a hydrochloric acid solution containing mannitol at a concentration shown in Table 2 was aliquoted in an amount shown in Table 2, and further, each stock solution of [$^{18}$F] FACBC shown in above Table 1 was wholly poured and mixed therein.

TABLE 2

A mannitol-containing hydrochloric acid solution added in each experiment and its addition amount

|  | Added mannitol-containing hydrochloric acid solution | | Addition amount of solution [mL] | Concentration of added hydrochloric acid [mmol/L] |
| --- | --- | --- | --- | --- |
|  | Concentration of mannitol [mmol/L] | Concentration of hydrochloric acid [mmol/L] | | |
| Example 1 | 396.6 | 41.9 | 0.86 | 0.57 |
| Example 2 | 662.2 | 101.9 | 0.49 | 0.67 |
| Example 3 | 272.3 | 53.9 | 1.2 | 0.98 |
| Example 4 | 276.9 | 53.4 | 1.2 | 1.1 |
| Example 5 | 554.6 | 333.1 | 0.60 | 2.8 |
| Example 6 | 550.1 | 338.5 | 0.59 | 2.5 |
| Example 7 | 426.7 | 39.0 | 0.78 | 0.40 |

*Concentration of added hydrochloric acid is indicated as a concentration which resulted after the completion of the dilution step To the solution obtained in the above step, a physiological saline solution containing mannitol at a concentration shown in Table 3 was added in an amount shown in Table 3 to make a sample solution. Meanwhile, each sample solution was prepared to have a mannitol concentration of 10 mmol/L.

TABLE 3

Content of mannitol in a mannitol-containing physiological saline solution used in the dilution step, addition amount of the physiological saline solution, and amount of the solution after the dilution step

|  | Content of mannitol [mmo/L] | Addition amount of solution [mL] | Amount of the solution after the dilution step [mL] |
| --- | --- | --- | --- |
| Example 1 | 6.08 | 47.5 | 63.0 |
| Example 2 | 7.11 | 59.9 | 75.2 |
| Example 3 | 6.64 | 50.1 | 65.7 |
| Example 4 | 5.82 | 43.2 | 58.4 |
| Example 5 | 6.95 | 56.8 | 72.7 |
| Example 6 | 7.44 | 63.8 | 80.0 |
| Example 7 | 7.03 | 60.0 | 75.5 |

For each sample solution, a pH was measured using a pH meter (type: HM-30R, manufactured by DKK-TOA CORPORATION).

The results are shown in Table 4. As shown in Table 4, the samples (in Examples 1-7) of 10 mmol/L mannitol-containing final agent to which hydrochloric acid was added in an amount corresponding to 0.40-2.8 mmol/L had a pH value of 2.8-5.9 which was in the pH range having a radiolysis inhibition effect.

The above results have indicated that a final agent having a pH with a radiolysis inhibition effect can be prepared by adding a hydrochloric acid in an amount corresponding to 0.40-2.8 mmol per 1 L of a 10 mmol/L mannitol-containing final agent.

TABLE 4

|  | Concentration of hydrochloric acid [mmo/L] | pH |
| --- | --- | --- |
| Example 1 | 0.57 | 4.78 |
| Example 2 | 0.67 | 3.93 |

TABLE 4-continued

|  | Concentration of hydrochloric acid [mmo/L] | pH |
| --- | --- | --- |
| Example 3 | 0.98 | 3.53 |
| Example 4 | 1.1 | 3.51 |
| Example 5 | 2.8 | 2.75 |
| Example 6 | 2.5 | 2.77 |
| Example 7 | 0.40 | 5.86 |

*Concentration of added hydrochloric acid is indicated as a concentration which resulted after the completion of the dilution step Example 8-12, Comparative Example 1

A stock solution of [$^{18}$F] FACBC was prepared in the same manner as in Example 1, and was left at room temperature for not less than 72 hours so as to attenuate radioactivity.

This solution was respectively aliquoted in an amount of 1.0 mL (Examples 8-9), 1.5 mL (Examples 10-12) and 2.5 mL (Comparative Example 1), and a hydrochloric acid solution containing mannitol at a concentration shown in Table 5 was added thereto in an amount shown in Table 5, followed by mixing.

TABLE 5

A mannitol-containing hydrochloric acid solution added in each experiment and its addition amount

|  | Added mannitol-containing hydrochloric acid solution | | Addition amount of solution [mL] | Concentration of added hydrochloric acid [mmol/L] |
| --- | --- | --- | --- | --- |
|  | Concentration of mannitol [mmol/L] | Concentration of hydrochloric acid [mmol/L] | | |
| Example 8 | 229.0 | 58.0 | 0.090 | 2.4 |
| Example 9 | 269.2 | 54.2 | 0.077 | 1.9 |
| Example 10 | 360.0 | 45.4 | 0.087 | 0.52 |
| Example 11 | 381.0 | 43.4 | 0.082 | 0.47 |
| Example 12 | 404.6 | 41.1 | 0.078 | 0.42 |
| Comparative Example 1 | 434.3 | 38.3 | 0.120 | 0.37 |

*Concentration of added hydrochloric acid is indicated as a concentration which resulted after the completion of the dilution step To the solution obtained in the above step, a physiological saline solution containing mannitol at a concentration shown in Table 6 was added in an amount shown in Table 6 to make a sample solution. Meanwhile, each sample solution was prepared to have a mannitol concentration of 10 mmol/L.

TABLE 6

Content of mannitol in a mannitol-containing physiological saline solution used in the dilution step, addition amount of the physiological saline solution, and amount of the solution after the dilution step

|  | Content of mannitol [mmo/L] | Addition amount of solution [mL] | Amount of the solution after the dilution step [mL] |
| --- | --- | --- | --- |
| Example 8 | 0.00 | 1.1 | 2.17 |
| Example 9 | 0.00 | 1.1 | 2.15 |
| Example 10 | 7.33 | 6.0 | 7.55 |
| Example 11 | 7.33 | 6.0 | 7.54 |
| Example 12 | 7.33 | 6.0 | 7.54 |
| Comparative Example 1 | 7.30 | 10.0 | 12.56 |

The results are shown in Table 7. As shown in Table 7, the samples (in Examples 8-12) of 10 mmol/L mannitol-containing final agent to which hydrochloric acid was added in an amount corresponding to 0.42-2.4 mmol/L had a pH value of 2.9-5.3 which was in the pH range having a radiolysis inhibition effect. On the other hand, the sample (in Comparative Example 1) of 10 mmol/L mannitol-containing final agent to which hydrochloric acid was added in an amount corresponding to 0.37 mmol/L had a pH value of 6.0 which was outside the pH range having a radiolysis inhibition effect.

TABLE 7

|  | Concentration of hydrochloric acid [mmo/L] | pH |
| --- | --- | --- |
| Example 8 | 2.4 | 2.90 |
| Example 9 | 1.9 | 3.09 |
| Example 10 | 0.52 | 4.30 |
| Example 11 | 0.47 | 4.72 |
| Example 12 | 0.42 | 5.31 |
| Comparative Example 1 | 0.37 | 5.96 |

*Concentration of added hydrochloric acid is indicated as a concentration which resulted after the completion of the dilution step Reference Examples 1-16, Comparative Examples 2-6

Relationship Between pH and Decrease of Radiochemical Purity

[$^{18}$F] fluoride ion-containing H$_2$$^{18}$O was allowed to pass through an anion-exchange column to adsorb and collect [$^{18}$F] fluoride ion on the column. Then, the column was washed with water, and a mixed solution composed of [$^{18}$F] fluoride ion, a potassium carbonate solution and a phase transfer catalyst was obtained in accordance with an ordinary method (for example, a method described in the references (Radioisotopes, 50, (2001), p. 205-227; Radioisotopes, 50, (2001), p. 228-256; "Production and quality control of radioactive agents for PET—Handbook of synthesis and clinical use—(2$^{nd}$ edition)", edited by PET Chemistry Workshop).

After the obtained mixed solution was heated in a reaction vessel to evaporate water to dryness, a solution of cis-1-(N-tert-butoxycarbonyl)amino-3-[(trifluoromethyl)sulfonyloxy]-cyclobutane carboxylic acid ethyl ester in acetonitrile was added thereto. The obtained solution was heated under stirring so as not to evaporate acetonitrile, thereby allowing nucleophilic substitution reaction to proceed to obtain a [$^{18}$F] fluorine-labeled compound.

After the reaction vessel was cooled to about 40° C., water for injection was added to the reaction solution for dilution, and the mixture was passed through a reversed phase column to collect the [$^{18}$F] fluorine-labeled compound. This column was washed, and flashed with a flow of helium gas. Then, the column was charged with a 4 mol/L sodium hydroxide solution, and the outlet of the column was closed. After three minutes passed, the outlet was opened to elute an alkali solution from the column and collect it in a vial. This operation was repeated twice. Then, the column was washed with water, and the washing was combined with the above-collected alkali solutions.

Next, to the above-collected solution, hydrochloric acid was added, and the mixture was heated to about 60° C. to effect deprotection reaction. The mixture was then passed through an ion retardation column, an alumina column and a reversed phase column in this order to perform purification and obtain a stock solution of anti-[$^{18}$F]-FACBC. Meanwhile, a hydrochloric acid solution was previously placed in a vessel which received the stock solution of anti-[$^{18}$F]-FACBC, so that the pH of the stock solution of anti-[$^{18}$F]-FACBC was adjusted to about 3.5.

Radioactivity of the obtained stock solution of anti-[$^{18}$F]-FACBC was measured, and then the stock solution was diluted with a physiological saline solution so as to have a radioactive concentration of about 510 MBq/mL at the time when experiment was initiated (0 hour in Table 9). 2.23 mL of this solution was aliquoted in a vial of 5 mL in volume, and a predetermined amount of a predetermined solution indicated in Table 8 was added thereto, to obtain a sample solution. The radioactive concentration of the sample solutions at the end of preparation was 653-686 MBq/mL.

TABLE 8

The solution added to each sample solution and pH at the end of preparation

| | Added solution (addition amount) | pH at the end of preparation |
|---|---|---|
| Reference Example 1 | 500 mmol/L HCl (40 µL) | 2.00 |
| Reference Example 2 | 500 mmol/L HCl (40 µL), physiological saline solution (40 µL) | 2.05 |
| Reference Example 3 | 100 mmol/L HCl (50 µL) | 2.66 |
| Reference Example 4 | physiological saline solution (80 µL) | 3.41 |
| Reference Example 5 | physiological saline solution (50 µL) | 3.46 |
| Reference Example 6 | 11 mmol/L NaOH (70 µL), physiological saline solution (10 µL) | 3.97 |
| Reference Example 7 | 10 mmol/L NaOH (70 µL) | 4.04 |
| Reference Example 8 | 12 mmol/L NaOH (70 µL), physiological saline solution (10 µL) | 4.55 |
| Reference Example 9 | 11 mmol/L NaOH (70 µL) | 4.58 |
| Reference Example 10 | 12 mmol/L NaOH (70 µL) | 4.88 |
| Reference Example 11 | 17 mmol/L NaOH (60 µL), physiological saline solution (20 µL) | 5.03 |
| Reference Example 12 | 13 mmol/L NaOH (70 µL) | 5.11 |
| Reference Example 13 | 15 mmol/L NaOH (70 µL), physiological saline solution (10 µL) | 5.46 |
| Reference Example 14 | 14.3 mmol/L NaOH (60 µL) | 5.54 |
| Reference Example 15 | 17 mmol/L NaOH (70 µL), physiological saline solution (10 µL) | 5.90 |
| Reference Example 16 | 14 mmol/L NaOH (70 µL) | 5.94 |
| Comparative Example 2 | 18.5 mmol/L NaOH (60 µL), physiological saline solution (20 µL) | 6.28 |
| Comparative Example 3 | 14.1 mmol/L NaOH (70 µL) | 6.31 |
| Comparative Example 4 | 16 mmol/L NaOH (80 µL), physiological saline solution (10 µL) | 6.57 |
| Comparative Example 5 | 15 mmol/L NaOH (70 µL) | 6.83 |
| Comparative Example 6 | 17 mmol/L NaOH (80 µL), physiological saline solution (0 µL) | 7.70 |

The sample solution was stored in an electric thermostatic chamber adjusted to 25° C., and was then subjected to TLC analysis which was performed on the following conditions at the time of initiation of the experiment (0 hour) and 8.5 hours after the initiation of the experiment. Values of radiochemical purity were calculated in accordance with the following equation (1). Measurement of the radiochemical purity was repeated three times for each sample solution.

TLC analysis conditions:
Mobile phase: acetonitrile/water/100% acetic acid=4/1/1
TLC plate: Silica Gel 60F$_{254}$ (trade name, thickness: 0.25 mm, manufactured by Merck & Co., Inc.)
Mobile length: 10 cm
TLC scanner: Rita Star (manufactured by Raytest)
Number of analysis: Three times $$\text{Radiochemical purity (\%)} = \frac{\text{Radioactivity of } [^{18}F]FACBC \text{ peak}}{\text{Total radioactivity on } TLC \text{ plate}} \times 100 \quad (1)$$

The results are shown in Table 9 and FIG. 1.

TABLE 9

Changes of radiochemical purity and decrease of radiochemical purity of anti-[$^{18}$F]-FACBC solution at each pH

| | | Radiochemical purity (%) | | Decrease* (%) |
|---|---|---|---|---|
| | pH | 0 hour | 8.5 hours | 8.5 hours |
| Reference Example 1 | 2.00 | 99.41 | 99.44 | 0.03 |
| Reference Example 2 | 2.05 | 99.59 | 99.42 | −0.17 |
| Reference Example 3 | 2.66 | 99.38 | 99.33 | −0.05 |
| Reference Example 4 | 3.41 | 99.51 | 99.21 | −0.30 |
| Reference Example 5 | 3.46 | 99.39 | 99.26 | −0.13 |
| Reference Example 6 | 3.97 | 99.48 | 99.02 | −0.46 |
| Reference Example 7 | 4.04 | 99.38 | 99.11 | −0.27 |
| Reference Example 8 | 4.55 | 99.56 | 99.01 | −0.55 |
| Reference Example 9 | 4.58 | 99.35 | 98.98 | −0.37 |
| Reference Example 10 | 4.88 | 99.44 | 99.07 | −0.37 |
| Reference Example 11 | 5.03 | 99.46 | 98.89 | −0.57 |

TABLE 9-continued

Changes of radiochemical purity and decrease of radiochemical purity of anti-[$^{18}$F]-FACBC solution at each pH

| | pH | Radiochemical purity (%) | | Decrease* (%) |
| --- | --- | --- | --- | --- |
| | | 0 hour | 8.5 hours | 8.5 hours |
| Reference Example 12 | 5.11 | 99.51 | 98.93 | −0.58 |
| Reference Example 13 | 5.46 | 99.52 | 99.06 | −0.46 |
| Reference Example 14 | 5.54 | 99.49 | 99.03 | −0.46 |
| Reference Example 15 | 5.90 | 99.51 | 98.86 | −0.65 |
| Reference Example 16 | 5.94 | 99.45 | 98.93 | −0.52 |
| Comparative Example 2 | 6.28 | 99.53 | 98.81 | −0.72 |
| Comparative Example 3 | 6.31 | 99.37 | 98.80 | −0.57 |
| Comparative Example 4 | 6.57 | 99.43 | 98.67 | −0.76 |
| Comparative Example 5 | 6.83 | 99.32 | 98.35 | −0.97 |
| Comparative Example 6 | 7.70 | 99.37 | 97.31 | −2.06 |

*Decrease (%) = (radiochemical purity after 8.5 hours) − (radiochemical purity after 0 hour)

Referring to the relation between the pH and the decrease of radiochemical purity, relatively mild decrease of radiochemical purity was observed with the pH increase from 2.00 to 5.94. The slope based on linear approximation was calculated, and as a result, the slope was −0.145 in the pH range of 2.00-4.88, and was −0.010 in the pH range of 5.03-5.94.

On the other hand, when the pH value was not less than 6.28, sharp decrease of radiochemical purity occurred with the pH increase. The slope based on linear approximation was calculated, and as a result, it was −1.000. This value was about 6.7 times the value in the pH range of 2.00-4.88, and about 100 times the value in the pH range of 5.03-5.94. These have indicated that when the pH value is not less than 6.28, a drastic decrease of radiochemical purity occurs compared with the pH range of 2.00-5.94.

Reference Examples 17-28

Relation Between Mannitol Concentration and Radiochemical Purity at pH Values of 3.44 and 4.78

A stock solution of anti-[$^{18}$F]-FACBC was prepared from [$^{18}$F] fluoride ion-containing H$_2$$^{18}$O in the same manner as in Reference Example 1. Then, to the prepared stock solution of anti-[$^{18}$F] FACBC, a hydrochloric acid and a physiological saline solution were added so as to have a radioactive concentration of about 500 MBq/mL and a pH value of about 4.8 at the time when experiment was initiated (0 hour in Table 11). 2.23 mL of the obtained solution was aliquoted in a vial of 5 mL in volume, and a mannitol solution or a hydrochloric acid at the concentration shown in Table 10 was added in an amount shown in Table 10 to obtain a sample solution. The radioactive concentration of the sample solution at the end of preparation was 553-565 MBq/mL.

TABLE 10

Addition amount of mannitol solution in each sample solution

| | pH | Added solution (addition amount) | Mannitol concentration at the end of preparation (μmol/mL) |
| --- | --- | --- | --- |
| Reference Example 17 | 3.44 | Mannitol 0.83 mg/mL solution (50 μL) 40 mmol/L HCl (20 μL) | 0.1 |
| Reference Example 18 | 3.44 | Mannitol 4.17 mg/mL solution (50 μL) 40 mmol/L HCl (20 μL) | 0.5 |
| Reference Example 19 | 3.44 | Mannitol 8.34 mg/mL solution (50 μL) 40 mmol/L HCl (20 μL) | 1.0 |
| Reference Example 20 | 3.44 | Mannitol 41.72 mg/mL solution (50 μL) 40 mmol/L HCl (20 μL) | 5.0 |
| Reference Example 21 | 3.44 | Mannitol 83.43 mg/mL solution (50 μL) 40 mmol/L HCl (20 μL) | 10.0 |
| Reference Example 22 | 3.44 | Mannitol 166.87 mg/mL solution (50 μL) 40 mmol/L HCl (20 μL) | 20.0 |
| Reference Example 23 | 4.78 | Mannitol 0.83 mg/mL solution (50 μL) | 0.1 |
| Reference Example 24 | 4.78 | Mannitol 4.17 mg/mL solution (50 μL) | 0.5 |
| Reference Example 25 | 4.78 | Mannitol 8.34 mg/mL solution (50 μL) | 1.0 |
| Reference Example 26 | 4.78 | Mannitol 41.72 mg/mL solution (50 μL) | 5.0 |
| Reference Example 27 | 4.78 | Mannitol 83.43 mg/mL solution (50 μL) | 10.0 |
| Reference Example 28 | 4.78 | Mannitol 166.87 mg/mL solution (50 μL) | 20.0 |

The sample solution was stored in an electric thermostatic chamber adjusted to 25° C., and the value of radiochemical purity was calculated in the same manner as in Reference Example 1 at the time of initiation of the experiment (0 hour) and 8.5 hours after the initiation of the experiment. Measurement of the radiochemical purity was repeated three times for each sample solution.

The results are shown in Table 11 and FIG. 2. In all the Reference Examples at the pH values of 3.44 and 4.78, decrease of radiochemical purity was drastically inhibited with increase of mannitol concentration, and the reduction effect was saturated at a mannitol concentration of not less than 5.0 μmol/mL.

Also, the decrease of radiochemical purity was more inhibited at both mannitol concentrations at the pH value of 3.44 than 4.78.

From the above results, it was confirmed that the pH value of the solution contributes to radiochemical stability. Also, it was shown that radiolysis can be additionally reduced by adding mannitol.

TABLE 11

Changes of radiochemical purity and decrease of radiochemical purity of anti-[$^{18}$F]-FACBC solution in the presence of mannitol

| | | Mannitol | Radiochemical purity (%) | | Decrease* (%) |
| --- | --- | --- | --- | --- | --- |
| | pH | Concentration (μmol/mL) | 0 hour | 8.5 hours | 8.5 hours |
| Reference Example 17 | 3.44 | 0.1 | 99.38 | 99.10 | −0.28 |

TABLE 11-continued

Changes of radiochemical purity and decrease of radiochemical purity of anti-[$^{18}$F]-FACBC solution in the presence of mannitol

| | pH | Mannitol Concentration (μmol/mL) | Radiochemical purity (%) 0 hour | Radiochemical purity (%) 8.5 hours | Decrease* (%) 8.5 hours |
|---|---|---|---|---|---|
| Reference Example 18 | 3.44 | 0.5 | 99.46 | 99.22 | −0.24 |
| Reference Example 19 | 3.44 | 1.0 | 99.39 | 99.25 | −0.14 |
| Reference Example 20 | 3.44 | 5.0 | 99.47 | 99.42 | −0.05 |
| Reference Example 21 | 3.44 | 10.0 | 99.42 | 99.33 | −0.09 |
| Reference Example 22 | 3.44 | 20.0 | 99.47 | 99.41 | −0.06 |
| Reference Example 23 | 4.78 | 0.1 | 99.39 | 98.93 | −0.46 |
| Reference Example 24 | 4.78 | 0.5 | 99.47 | 99.09 | −0.38 |
| Reference Example 25 | 4.78 | 1.0 | 99.38 | 99.14 | −0.24 |
| Reference Example 26 | 4.78 | 5.0 | 99.45 | 99.30 | −0.15 |
| Reference Example 27 | 4.78 | 10.0 | 99.41 | 99.26 | −0.15 |
| Reference Example 28 | 4.78 | 20.0 | 99.46 | 99.27 | −0.19 |

*Decrease (%) = (radiochemical purity after 8.5 hours) − (radiochemical purity after 0 hour)

Figure 1:
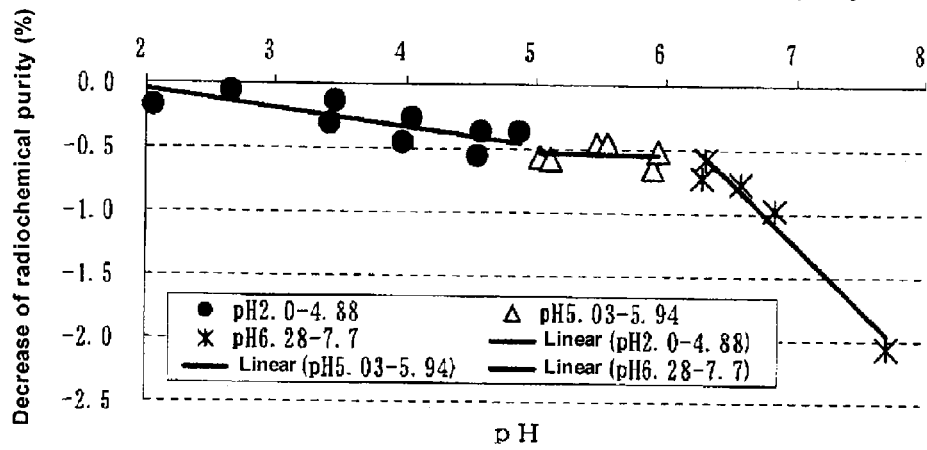
FIG. 1 is a graph which shows a relation between the pH and the decrease of radiochemical purity.
Figure 2:
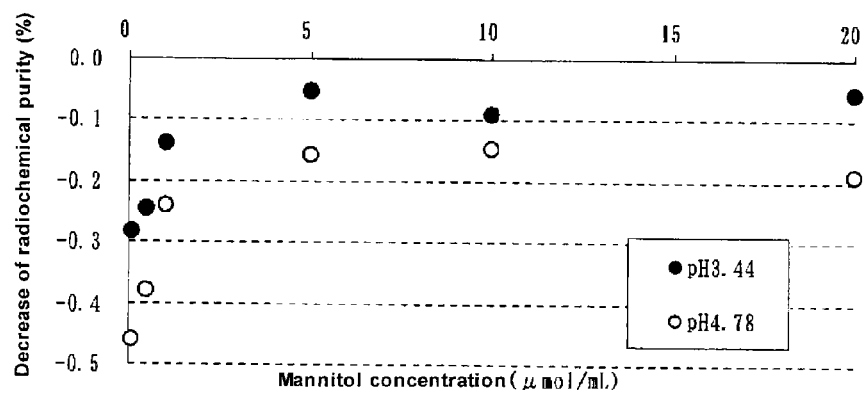
FIG. 2 is a graph which shows a elation between the mannitol concentration and the decrease of radiochemical purity.

The invention claimed is:

1. A method for producing a radioactive diagnostic imaging agent containing a radioactive $^{18}$fluorine-labeled organic compound represented by the following formula (1):

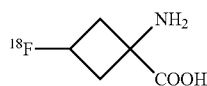 (1)

which comprises
a first step of providing a solution containing the radioactive $^{18}$fluorine-labeled organic compound represented by the above formula (1),
a second step of adding hydrochloric acid to the solution obtained in the first step in an amount sufficient for the solution to be kept within a pH of 2.0-5.9 in the following third step, and
a third step of diluting the solution obtained in the second step in order to adjust the solution to a desired radioactive concentration within a pH of 2.0-5.9, whereby said radioactive diagnostic imaging agent is obtained,
wherein in the second step the hydrochloric acid is added in an amount corresponding to 0.4-2.8 mmol per 1 L of the solution in the third step.

2. The method of claim 1, wherein the third step comprises adding water, a physiological saline solution or a Ringer's solution obtained in the second step.

3. The method of claim 1, wherein the hydrochloric acid is added in the second step in an amount corresponding to 0.52-2.8 mmol per 1 L of the solution in the third step.

4. A method for producing a radioactive diagnostic imaging agent containing a radioactive $^{18}$fluorine-labeled organic compound represented by the following formula (1):

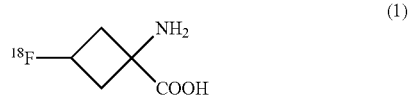 (1)

which comprises
a first step of providing a solution containing the radioactive $^{18}$fluorine-labeled organic compound represented by the above formula (1),
a second step of adding hydrochloric acid to the solution obtained in the first step in an amount sufficient for the solution to be kept within a pH of 2.0-4.9 in the following third step, and
a third step of diluting the solution obtained in the second step in order to adjust the solution to a desired radioactive concentration within a pH of 2.0-4.9, whereby said radioactive diagnostic imaging agent is obtained,
wherein in the second step the hydrochloric acid is added in an amount corresponding to 0.4-2.8 mmol per 1 L of the solution in the third step.

5. The method according to claim 4, wherein the hydrochloric acid is added in the second step in an amount corresponding to 0.52-2.8 mmol per 1 L of the solution in the third step.

* * * * *